(12) United States Patent
Möckel et al.

(10) Patent No.: US 7,759,056 B2
(45) Date of Patent: Jul. 20, 2010

(54) NUCLEOTIDE SEQUENCE ENCODING THE DAPC GENE AND PROCESS FOR THE PRODUCTION OF L-LYSINE

(75) Inventors: Bettina Möckel, Düsseldorf (DE); Anke Weissenborn, Tübingen (DE); Walter Pfefferle, Halle(Westf.) (DE); Michael Hartmann, Bielefeld (DE); Jörn Kalinowski, Bielefeld (DE); Alfred Pühler, Bielefeld (DE)

(73) Assignee: Evonik Degussa GmbH, Essen (DE)

( * ) Notice: Subject to any disclaimer, the term of this patent is extended or adjusted under 35 U.S.C. 154(b) by 636 days.

(21) Appl. No.: 10/745,684

(22) Filed: Dec. 29, 2003

(65) Prior Publication Data

US 2005/0100927 A1    May 12, 2005

Related U.S. Application Data

(62) Division of application No. 09/813,919, filed on Mar. 22, 2001, now Pat. No. 6,740,742.

(30) Foreign Application Priority Data

Mar. 23, 2000    (DE)    ................ 100 14 546

(51) Int. Cl.
    *C12Q 1/68*    (2006.01)
    *C12P 13/08*    (2006.01)
(52) U.S. Cl. .......................... 435/6; 435/115
(58) Field of Classification Search ............ None
    See application file for complete search history.

(56) References Cited

U.S. PATENT DOCUMENTS

| 4,954,441 | A | * | 9/1990 | Katsumata et al. | ........... | 435/115 |
| 6,040,160 | A | * | 3/2000 | Kojima et al. | ............... | 435/115 |
| 2003/0049804 | A1 | | 3/2003 | Pompejus et al. | | |

FOREIGN PATENT DOCUMENTS

| EP | 1 108 790 | 6/2001 |
| WO | WO 01/00843 | 1/2001 |

OTHER PUBLICATIONS

Mickle et al. 2000 Med. Clin. North Am. vol. 84 p. 597-607.*
Sjoden et al. 1998 International Journal of Systematic Bacteriology VO. 48 p. 69-74.*
GenBank Accession No. NC_006958 NCBI Website. Jun. 21, 2007. NOTE only pgs. 1, 226, and 394 are provided.*
Sahm et al. (Annals New York Academy of Sciences 1996 vol. 782 p. 25).*
Ledwidge et al. Biochemistry 1999 vol. 38 p. 3019.*
Schrumpf et al. (Journal of Bacteriology vol. 173 Jul. 1999 p. 4510).*
Cole et al., "Mycobacterium Tuberculosis H37Rv Complete Genome," *Database EMBL*, Dec. 6, 1997, XP-002256933.
Daiho et al., "Deletions or Specific Substitutions of a Few Residues in the NH$_2$-terminal Region (Ala$^3$ to Thr$^9$) of Sarcoplasmic Reticulum Ca$^{2+}$-ATPase Cause Inactivation and Rapid Degradation of the Enzyme Expressed in COS-1 Cells," *The Journal of Biological Chemistry*, vol. 274, No. 34, Aug. 20, 1999, pp. 23910-23915.
Fuchs et al., "Characterization of a *Bordetella pertussis* Diaminopimelate (DAP) Biosynthesis Locus Identifies dapC, a Novel Gene Coding for an N-Succinyl-L,LDAP Aminotransferase," *Journal of Bacteriology*, vol. 182, No. 13, Jul. 2000, pp. 3626-3631.
Ledwidge et al., "The Dual Biosynthetic Capability of N-Acetylornithine Aminotransferase in Arginine and Lysine Biosynthesis," *Biochemistry*, vol. 38, No. 10, 1999, pp. 3019-3024.
Mahairas et al., "Sequence-Tagged Connectors: A Sequence Approach to Mapping and Scanning the Human Genome," *Proc. Natl. Acad. Sci.*, vol. 96, No. 17, 1999, pp. 9739-9744.
Nishihara et al., "α(1,3/1,4) Fucosyltransferase (FucT-III) Gene is Inactivated by a Single Amino Acid Substitution in Lewis Histo-Blood Type Negative Individuals," *Biochemical and Biophysical Research Communications*, vol. 196, No. 2, Oct. 29, 1993, pp. 624-631.
Sahm et al., "Construction of L-Lysine-, L-Threonine-, or L-Isoleucine-Overproducing Strains of *Corynebacterium glutamicum*," *Annals New York Academy of Sciences*, vol. 782, 1996, pp. 25-39.
UnitProtKB/Swiss-Prot Entry No. P0A9D2, Oct. 23, 1986.
Schrumpf et al., "A Functionally Split Pathway for Lysine Synthesis In Corynebacterium Glutamicum," Journal of Bacteriology, 1991, 1733: 4510-4516.
Peterkofsky et al., "N-Succinyl-Ldiaminopimelic-glutamic Transaminase," Journal of Biological Chemistry, May 1961, vol. 236, No. 5, pp. 1432-1438.
IUBMB Enzyme Nomenclature EC 2.6.1.17. <http://www.chem.qmul.ac.uk/iubmb/enzyme/EC2/6/1/7.html>.

* cited by examiner

*Primary Examiner*—Sarae Bausch
*Assistant Examiner*—Katherine Salmon
(74) *Attorney, Agent, or Firm*—Pillsbury Winthrop Shaw Pittman LLP (57) ABSTRACT

The invention relates to an isolated polynucleotide from coryneform bacteria containing at least one polynucleotide sequence selected from the group consisting of a) polynucleotide which is at least 70% identical to a polynucleotide which encodes a polypeptide containing the amino acid sequence according to SEQ ID no. 2, b) polynucleotide which encodes a polypeptide which contains an amino acid sequence which is at least 70% identical to the amino acid sequence of SEQ ID no. 2, c) polynucleotide which is complementary to the polynucleotides of a) or b), and d) polynucleotide containing at least 15 successive nucleotides of the polynucleotide sequences of a), b) or c), and to a process for the fermentative production of L-amino acids, in particular L-lysine.

9 Claims, 2 Drawing Sheets

Figure 1: pEC-XT99A

Figure 2: pXT-dapCexp

SEQUENCE LISTING

```
<160> NUMBER OF SEQ ID NOS: 6

<210> SEQ ID NO 1
<211> LENGTH: 1300
<212> TYPE: DNA
<213> ORGANISM: Corynebacterium glutamicum
<220> FEATURE:
<221> NAME/KEY: CDS
<222> LOCATION: (91)..(1191)
<223> OTHER INFORMATION: dapC-Gene

<400> SEQUENCE: 1
gggctcccca ggtggtgcgg ctaagcttgg accacaagat tttgatcacc caatgatcgc          60
tgcgctgccg cctcaggcat aatctaacgc atg acc tct cgc acc ccg ctt gtt         114
                                 Met Thr Ser Arg Thr Pro Leu Val
                                   1               5 tct gtt ctt cct gat ttt ccg tgg gat tcg ctc gct tcc gca aaa gcc         162
Ser Val Leu Pro Asp Phe Pro Trp Asp Ser Leu Ala Ser Ala Lys Ala
         10                  15                  20 aaa gct gcg tct cac ccg gat ggg atc gtg aat ctt tct gtt ggc act         210
Lys Ala Ala Ser His Pro Asp Gly Ile Val Asn Leu Ser Val Gly Thr
 25                  30                  35                  40 ccg gtt gat ccg gtc gcg ccc agc att cag atc gcg ttg gca gaa gca         258
Pro Val Asp Pro Val Ala Pro Ser Ile Gln Ile Ala Leu Ala Glu Ala
                 45                  50                  55 gcg ggg ttt tcg ggt tac cct caa acc atc ggc acc ccg gaa ctc cgc         306
Ala Gly Phe Ser Gly Tyr Pro Gln Thr Ile Gly Thr Pro Glu Leu Arg
             60                  65                  70 gca gcc atc agg ggc gcg ctt gag cgg cgc tac aac atg aca aag ctt         354
Ala Ala Ile Arg Gly Ala Leu Glu Arg Arg Tyr Asn Met Thr Lys Leu
         75                  80                  85 gtc gac gcc tcc ctc ctc ccc gtc gtg ggt acc aag gag gca att gcc         402
Val Asp Ala Ser Leu Leu Pro Val Val Gly Thr Lys Glu Ala Ile Ala
 90                  95                 100 ctt ctt cca ttc gcg ttg ggt att tcc ggc acc gtt gtc atc cca gag         450
Leu Leu Pro Phe Ala Leu Gly Ile Ser Gly Thr Val Val Ile Pro Glu
105                 110                 115                 120 att gcg tac cca acc tac gaa gtc gct gtc gtg gcc gca gga tgc acc         498
Ile Ala Tyr Pro Thr Tyr Glu Val Ala Val Val Ala Ala Gly Cys Thr
                125                 130                 135
```

```
gtg ttg cgt tct gat tcg ctg ttt aag ctc ggc ccg cag atc ccg tcg   546
Val Leu Arg Ser Asp Ser Leu Phe Lys Leu Gly Pro Gln Ile Pro Ser
            140                 145                 150 atg atg ttt atc aac tca cca tcc aac ccc aca ggc aag gtt ctg ggc   594
Met Met Phe Ile Asn Ser Pro Ser Asn Pro Thr Gly Lys Val Leu Gly
                155                 160                 165 atc cca cac ttg cgc aag gtt gtg aag tgg gcg cag gaa aac aac gtg   642
Ile Pro His Leu Arg Lys Val Val Lys Trp Ala Gln Glu Asn Asn Val
        170                 175                 180 atc ctc gca gct gat gaa tgc tac ttg ggt ctt ggc tgg gac gat gaa   690
Ile Leu Ala Ala Asp Glu Cys Tyr Leu Gly Leu Gly Trp Asp Asp Glu
185                 190                 195                 200 aac cca ccg atc tca att ttg gat cca cgt gtc tgc gat ggc gac cac   738
Asn Pro Pro Ile Ser Ile Leu Asp Pro Arg Val Cys Asp Gly Asp His
                205                 210                 215 acc aac ttg atc gcc att cac tcg ctg tct aaa acc tca aac ctc gct   786
Thr Asn Leu Ile Ala Ile His Ser Leu Ser Lys Thr Ser Asn Leu Ala
            220                 225                 230 tct tac cgc gca ggt tac ctc gtt ggc gat cca gcg ctg att ggt gaa   834
Ser Tyr Arg Ala Gly Tyr Leu Val Gly Asp Pro Ala Leu Ile Gly Glu
                235                 240                 245 ctc acg gaa gtc cgt aag aac ttg ggt ctc atg gtt cct ttc cca atc   882
Leu Thr Glu Val Arg Lys Asn Leu Gly Leu Met Val Pro Phe Pro Ile
        250                 255                 260 cag cag gcc atg atc gca gcc ctc aac gac gat gac caa gag gca ggg   930
Gln Gln Ala Met Ile Ala Ala Leu Asn Asp Asp Asp Gln Glu Ala Gly
265                 270                 275                 280 cag aag ctc acc tac gcg att cgt cga gca aaa ctc atg cgc gcc ctg   978
Gln Lys Leu Thr Tyr Ala Ile Arg Arg Ala Lys Leu Met Arg Ala Leu
                285                 290                 295 ttg gaa tcc ggc ttt cag gta gat aat tct gaa gcg gtt ctg tac ctc   1026
Leu Glu Ser Gly Phe Gln Val Asp Asn Ser Glu Ala Gly Leu Tyr Leu
            300                 305                 310 tgg gcg acg cgt gaa gaa cct tgc cgt gac act gtc gat tgg ttc gct   1074
Trp Ala Thr Arg Glu Glu Pro Cys Arg Asp Thr Val Asp Trp Phe Ala
                315                 320                 325 gag cgt ggc att ctc gtt gcc cca gga gac ttc tat ggc cct cgc gga   1122
Glu Arg Gly Ile Leu Val Ala Pro Gly Asp Phe Tyr Gly Pro Arg Gly
        330                 335                 340 gcg cag cat gtg cgt gtg gcg atg acc gaa acc gac gag cgc gtc gac   1170
Ala Gln His Val Arg Val Ala Met Thr Glu Thr Asp Glu Arg Val Asp
345                 350                 355                 360 gcc ttt gtt tct cgc ctg agc taaacacgac taagcttatt tgtttaatt       1221
Ala Phe Val Ser Arg Leu Ser
                365 gagtttgaag ttttccgtcg aaagaggcca tttgagttcc gagtccagtc ctgagtcgag   1281 taccgagcaa aaaacctgg                                               1300

<210> SEQ ID NO 2
<211> LENGTH: 367
<212> TYPE: PRT
<213> ORGANISM: Corynebacterium glutamicum

<400> SEQUENCE: 2

Met Thr Ser Arg Thr Pro Leu Val Ser Val Leu Pro Asp Phe Pro Trp
 1               5                  10                  15

Asp Ser Leu Ala Ser Ala Lys Ala Lys Ala Ala Ser His Pro Asp Gly
            20                  25                  30
```

```
Ile Val Asn Leu Ser Val Gly Thr Pro Val Asp Pro Val Ala Pro Ser
         35                  40                  45

Ile Gln Ile Ala Leu Ala Glu Ala Ala Gly Phe Ser Gly Tyr Pro Gln
 50                  55                  60

Thr Ile Gly Thr Pro Glu Leu Arg Ala Ala Ile Arg Gly Ala Leu Glu
 65                  70                  75                  80

Arg Arg Tyr Asn Met Thr Lys Leu Val Asp Ala Ser Leu Leu Pro Val
                 85                  90                  95

Val Gly Thr Lys Glu Ala Ile Ala Leu Leu Pro Phe Ala Leu Gly Ile
            100                 105                 110

Ser Gly Thr Val Val Ile Pro Glu Ile Ala Tyr Pro Thr Tyr Glu Val
            115                 120                 125

Ala Val Val Ala Ala Gly Cys Thr Val Leu Arg Ser Asp Ser Leu Phe
130                 135                 140

Lys Leu Gly Pro Gln Ile Pro Ser Met Met Phe Ile Asn Ser Pro Ser
145                 150                 155                 160

Asn Pro Thr Gly Lys Val Leu Gly Ile Pro His Leu Arg Lys Val Val
                165                 170                 175

Lys Trp Ala Gln Glu Asn Asn Val Ile Leu Ala Ala Asp Glu Cys Tyr
            180                 185                 190

Leu Gly Leu Gly Trp Asp Asp Glu Asn Pro Pro Ile Ser Ile Leu Asp
            195                 200                 205

Pro Arg Val Cys Asp Gly Asp His Thr Asn Leu Ile Ala Ile His Ser
210                 215                 220

Leu Ser Lys Thr Ser Asn Leu Ala Ser Tyr Arg Ala Gly Tyr Leu Val
225                 230                 235                 240

Gly Asp Pro Ala Leu Ile Gly Glu Leu Thr Glu Val Arg Lys Asn Leu
                245                 250                 255

Gly Leu Met Val Pro Phe Pro Ile Gln Gln Ala Met Ile Ala Ala Leu
            260                 265                 270

Asn Asp Asp Asp Gln Glu Ala Gly Gln Lys Leu Thr Tyr Ala Ile Arg
            275                 280                 285

Arg Ala Lys Leu Met Arg Ala Leu Leu Glu Ser Gly Phe Gln Val Asp
290                 295                 300

Asn Ser Glu Ala Gly Leu Tyr Leu Trp Ala Thr Arg Glu Glu Pro Cys
305                 310                 315                 320

Arg Asp Thr Val Asp Trp Phe Ala Glu Arg Gly Ile Leu Val Ala Pro
                325                 330                 335

Gly Asp Phe Tyr Gly Pro Arg Gly Ala Gln His Val Arg Val Ala Met
            340                 345                 350

Thr Glu Thr Asp Glu Arg Val Asp Ala Phe Val Ser Arg Leu Ser
            355                 360                 365

<210> SEQ ID NO 3
<211> LENGTH: 1300
<212> TYPE: DNA
<213> ORGANISM: Corynebacterium glutamicum
<220> FEATURE:
<221> NAME/KEY: CDS
<222> LOCATION: (91)..(1191)
<223> OTHER INFORMATION: dapC-Allele

<400> SEQUENCE: 3
gggctcccca ggtggtgcgg ctaagcttgg accacaagat tttgatcacc caatgatcgc    60
tgcgctgccg cctcaggcat aatctaacgc atg acc tct cgc acc ccg ctt gtt   114
                                 Met Thr Ser Arg Thr Pro Leu Val
```

```
                                  1               5 tct gtt ctt cct gat ttt ccg tgg gat tcg ctc gct tcc gca aaa gcc        162
Ser Val Leu Pro Asp Phe Pro Trp Asp Ser Leu Ala Ser Ala Lys Ala
     10              15                  20 aaa gct gcg tct cac ccg gat ggg atc gtg aat ctt tct gtt ggc act        210
Lys Ala Ala Ser His Pro Asp Gly Ile Val Asn Leu Ser Val Gly Thr
 25              30                  35                  40 ccg gtt gat ccg gtc gcg ccc agc att cag atc gcg ttg gca gaa gca        258
Pro Val Asp Pro Val Ala Pro Ser Ile Gln Ile Ala Leu Ala Glu Ala
                 45                  50                  55 gcg ggg ttt tcg ggt tac cct caa acc atc ggc acc ccg gaa ctc cgc        306
Ala Gly Phe Ser Gly Tyr Pro Gln Thr Ile Gly Thr Pro Glu Leu Arg
             60                  65                  70 gca gcc atc agg ggc gcg ctt gag cgg cgc tac aac atg aca aag ctt        354
Ala Ala Ile Arg Gly Ala Leu Glu Arg Arg Tyr Asn Met Thr Lys Leu
         75                  80                  85 gtc gac gcc tcc ctc ctc ccc gtc gtg ggt acc aag gag gca att gcc        402
Val Asp Ala Ser Leu Leu Pro Val Val Gly Thr Lys Glu Ala Ile Ala
     90                  95                 100 ctt ctt cca ttc gcg ttg ggt att tcc ggc acc gtt gtc atc cca gag        450
Leu Leu Pro Phe Ala Leu Gly Ile Ser Gly Thr Val Val Ile Pro Glu
105                 110                 115                 120 att gcg tac cca acc tac gaa gtc gct gtc gtg gcc gca gga tgc acc        498
Ile Ala Tyr Pro Thr Tyr Glu Val Ala Val Val Ala Ala Gly Cys Thr
                125                 130                 135 gtg ttg cgt tct gat tcg ctg ttt aag ctc ggc ccg cag atc ccg tcg        546
Val Leu Arg Ser Asp Ser Leu Phe Lys Leu Gly Pro Gln Ile Pro Ser
            140                 145                 150 atg atg ttt atc aac tca cca tcc aac ccc aca ggc aag gtt ctg ggc        594
Met Met Phe Ile Asn Ser Pro Ser Asn Pro Thr Gly Lys Val Leu Gly
        155                 160                 165 atc cca cac ttg cgc aag gtt gtg aag tgg gcg cag gaa aac aac gtg        642
Ile Pro His Leu Arg Lys Val Val Lys Trp Ala Gln Glu Asn Asn Val
    170                 175                 180 atc ctc gca gct gat gaa tgc tac ttg ggt ctt ggc tgg gac gat gaa        690
Ile Leu Ala Ala Asp Glu Cys Tyr Leu Gly Leu Gly Trp Asp Asp Glu
185                 190                 195                 200 aac cca ccg atc tca att ttg gat cta cgt gtc tgc gat ggc gac cac        738
Asn Pro Pro Ile Ser Ile Leu Asp Leu Arg Val Cys Asp Gly Asp His
                205                 210                 215 acc aac ttg atc gcc att cac tcg ctg tct aaa acc tca aac ctc gct        786
Thr Asn Leu Ile Ala Ile His Ser Leu Ser Lys Thr Ser Asn Leu Ala
            220                 225                 230 tct tac cgc gca ggt tac ctc gtt ggc gat cca gcg ctg att ggt gaa        834
Ser Tyr Arg Ala Gly Tyr Leu Val Gly Asp Pro Ala Leu Ile Gly Glu
        235                 240                 245 ctc acg gaa gtc cgt aag aac ttg ggt ctc atg gtt cct ttc cca atc        882
Leu Thr Glu Val Arg Lys Asn Leu Gly Leu Met Val Pro Phe Pro Ile
    250                 255                 260 cag cag gcc atg atc gca gcc ctc aac gac gat gac caa gag gca ggg        930
Gln Gln Ala Met Ile Ala Ala Leu Asn Asp Asp Asp Gln Glu Ala Gly
265                 270                 275                 280 cag aag ctc acc tac gcg att cgt cga gca aaa ctc atg cgc gcc ctg        978
Gln Lys Leu Thr Tyr Ala Ile Arg Arg Ala Lys Leu Met Arg Ala Leu
                285                 290                 295 ttg gaa tcc ggc ttt cag gta gat aat tct gaa gcg ggt ctg tac ctc       1026
Leu Glu Ser Gly Phe Gln Val Asp Asn Ser Glu Ala Gly Leu Tyr Leu
            300                 305                 310 tgg gcg acg cgt gaa gaa cct tgc cgt gac act gtc gat tgg ttc gct       1074
```

-continued

```
Trp Ala Thr Arg Glu Glu Pro Cys Arg Asp Thr Val Asp Trp Phe Ala
        315                 320                 325 gag cgt ggc att ctc gtt gcc cca gga gac ttc tat ggc cct cgc gga      1122
Glu Arg Gly Ile Leu Val Ala Pro Gly Asp Phe Tyr Gly Pro Arg Gly
        330                 335                 340 gcg cag cat gtg cgt gtg gcg atg acc gaa acc gac gag cgc gtc gac      1170
Ala Gln His Val Arg Val Ala Met Thr Glu Thr Asp Glu Arg Val Asp
345                 350                 355                 360 gcc ttt gtt tct cgc ctg agc taaacacgac taagcttatt ttgtttaatt         1221
Ala Phe Val Ser Arg Leu Ser
                365 gagtttgaag ttttccgtcg aaagaggcca tttgagttcc gagtccagtc ctgagtcgag    1281 taccgagcaa aaaacctgg                                                 1300

<210> SEQ ID NO 4
<211> LENGTH: 367
<212> TYPE: PRT
<213> ORGANISM: Corynebacterium glutamicum

<400> SEQUENCE: 4

Met Thr Ser Arg Thr Pro Leu Val Ser Val Leu Pro Asp Phe Pro Trp
  1               5                  10                  15

Asp Ser Leu Ala Ser Ala Lys Ala Lys Ala Ala Ser His Pro Asp Gly
             20                  25                  30

Ile Val Asn Leu Ser Val Gly Thr Pro Val Asp Pro Val Ala Pro Ser
         35                  40                  45

Ile Gln Ile Ala Leu Ala Glu Ala Ala Gly Phe Ser Gly Tyr Pro Gln
     50                  55                  60

Thr Ile Gly Thr Pro Glu Leu Arg Ala Ala Ile Arg Gly Ala Leu Glu
 65                  70                  75                  80

Arg Arg Tyr Asn Met Thr Lys Leu Val Asp Ala Ser Leu Leu Pro Val
                 85                  90                  95

Val Gly Thr Lys Glu Ala Ile Ala Leu Leu Pro Phe Ala Leu Gly Ile
            100                 105                 110

Ser Gly Thr Val Val Ile Pro Glu Ile Ala Tyr Pro Thr Tyr Glu Val
        115                 120                 125

Ala Val Val Ala Ala Gly Cys Thr Val Leu Arg Ser Asp Ser Leu Phe
    130                 135                 140

Lys Leu Gly Pro Gln Ile Pro Ser Met Met Phe Ile Asn Ser Pro Ser
145                 150                 155                 160

Asn Pro Thr Gly Lys Val Leu Gly Ile Pro His Leu Arg Lys Val Val
                165                 170                 175

Lys Trp Ala Gln Glu Asn Asn Val Ile Leu Ala Ala Asp Glu Cys Tyr
            180                 185                 190

Leu Gly Leu Gly Trp Asp Asp Glu Asn Pro Pro Ile Ser Ile Leu Asp
        195                 200                 205

Leu Arg Val Cys Asp Gly Asp His Thr Asn Leu Ile Ala Ile His Ser
    210                 215                 220

Leu Ser Lys Thr Ser Asn Leu Ala Ser Tyr Arg Ala Gly Tyr Leu Val
225                 230                 235                 240

Gly Asp Pro Ala Leu Ile Gly Glu Leu Thr Glu Val Arg Lys Asn Leu
                245                 250                 255

Gly Leu Met Val Pro Phe Pro Ile Gln Gln Ala Met Ile Ala Ala Leu
            260                 265                 270

Asn Asp Asp Asp Gln Glu Ala Gly Gln Lys Leu Thr Tyr Ala Ile Arg
```

-continued

```
                275                 280                 285
Arg Ala Lys Leu Met Arg Ala Leu Leu Glu Ser Gly Phe Gln Val Asp
        290                 295                 300

Asn Ser Glu Ala Gly Leu Tyr Leu Trp Ala Thr Arg Glu Glu Pro Cys
305                 310                 315                 320

Arg Asp Thr Val Asp Trp Phe Ala Glu Arg Gly Ile Leu Val Ala Pro
                325                 330                 335

Gly Asp Phe Tyr Gly Pro Arg Gly Ala Gln His Val Arg Val Ala Met
                340                 345                 350

Thr Glu Thr Asp Glu Arg Val Asp Ala Phe Val Ser Arg Leu Ser
        355                 360                 365

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Primer
<220> FEATURE:
<223> OTHER INFORMATION: Primer DapC (dCex1)

<400> SEQUENCE: 5
gatctagaat tcgcctcagg cataatctaa cg                                  32

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Primer
<220> FEATURE:
<223> OTHER INFORMATION: Primer DapC (dCexna2)

<400> SEQUENCE: 6
gatctatcta gacagaggac aaggcaatcg ga                                  32
```

US 7,759,056 B2

NUCLEOTIDE SEQUENCE ENCODING THE DAPC GENE AND PROCESS FOR THE PRODUCTION OF L-LYSINE

This is a divisional of U.S. patent application Ser. No. 09/813,919, filed Mar. 22, 2001, which claims priority to German Patent Appl. No. 100 14 546.9, filed Mar. 23, 2000, the subject matter of which is hereby incorporated herein by reference.

BACKGROUND OF THE INVENTION

1. Field of the Invention

The invention provides nucleotide sequences encoding the dapC gene and a process for the fermentative production of L-lysine, using coryneform bacteria in which the dapC gene (N-succinylaminoketopimelate transaminase gene) is enhanced, in particular over-expressed.

2. Background Information

Amino acids, in particular L-lysine, are used in human medicine and in the pharmaceuticals industry, but in particular in animal nutrition.

It is known that amino acids are produced by fermentation of strains of coryneform bacteria, in particular *Corynebacterium glutamicum*. Due to their great significance, efforts are constantly being made to improve the production process. Improvements to the process may relate to measures concerning fermentation technology, for example stirring and oxygen supply, or to the composition of the nutrient media, such as for example sugar concentration during fermentation, or to working up of the product by, for example, ion exchange chromatography, or to the intrinsic performance characteristics of the microorganism itself.

The performance characteristics of these microorganisms are improved using methods of mutagenesis, selection and mutant selection. In this manner, strains are obtained which are resistant to antimetabolites, such as for example the lysine analogue S-(2-aminoethyl)cysteine, or are auxotrophic for regulatorily significant metabolites and produce L-amino acids, such as for example L-lysine.

For some years, methods of recombinant DNA technology have likewise been used to improve strains of *Corynebacterium* which produce amino acids by amplifying individual amino acid biosynthesis genes and investigating the effect on amino acid production. Review articles on this subject may be found inter alia in Kinoshita ("Glutamic Acid Bacteria", in: Biology of Industrial Microorganisms, Demain and Solomon (Eds.), Benjamin Cummings, London, UK, 1985, 115-142), Hilliger (BioTec 2, 40-44 (1991)), Eggeling (Amino Acids 6:261-272 (1994)), Jetten and Sinskey (Critical Reviews in Biotechnology 15, 73-103 (1995)) and Sahm et al. (Annuals of the New York Academy of Science 782, 25-39 (1996)).

SUMMARY OF THE INVENTION

It is an object of the invention to provide novel methods for the improved fermentative production of L-lysine.

DESCRIPTION OF THE INVENTION

L-lysine is used in human medicine, in the pharmaceuticals industry and in particular in animal nutrition. There is accordingly general interest in providing novel improved processes for the production of L-lysine.

Any subsequent mention of L-lysine or lysine should be taken to mean not only the base, but also salts, such as for example lysine monohydrochloride or lysine sulfate.

The invention provides an isolated polynucleotide from coryneform bacteria containing at least one polynucleotide sequence selected from the group a) polynucleotide which is at least 70% identical to a polynucleotide which encodes a polypeptide containing the amino acid sequence of SEQ ID no. 2,
b) polynucleotide which encodes a polypeptide which contains an amino acid sequence which is at least 70% identical to the amino acid sequence of SEQ ID no. 2,
c) polynucleotide which is complementary to the polynucleotides of a) or b), or
d) polynucleotide containing at least 15 successive nucleotides of the polynucleotide sequences of a), b) or c).

The invention also provides the polynucleotide according to claim 1, wherein it preferably comprises replicable DNA containing:

(i) the nucleotide sequence shown in SEQ ID no. 1, or
(ii) at least one sequence which matches the sequence (i) within the degeneration range of the genetic code, or
(iii) at least one sequence which hybridizes with the complementary sequence to sequence (i) or (ii) and optionally
(iv) functionally neutral sense mutations in (i).

Figure 2:
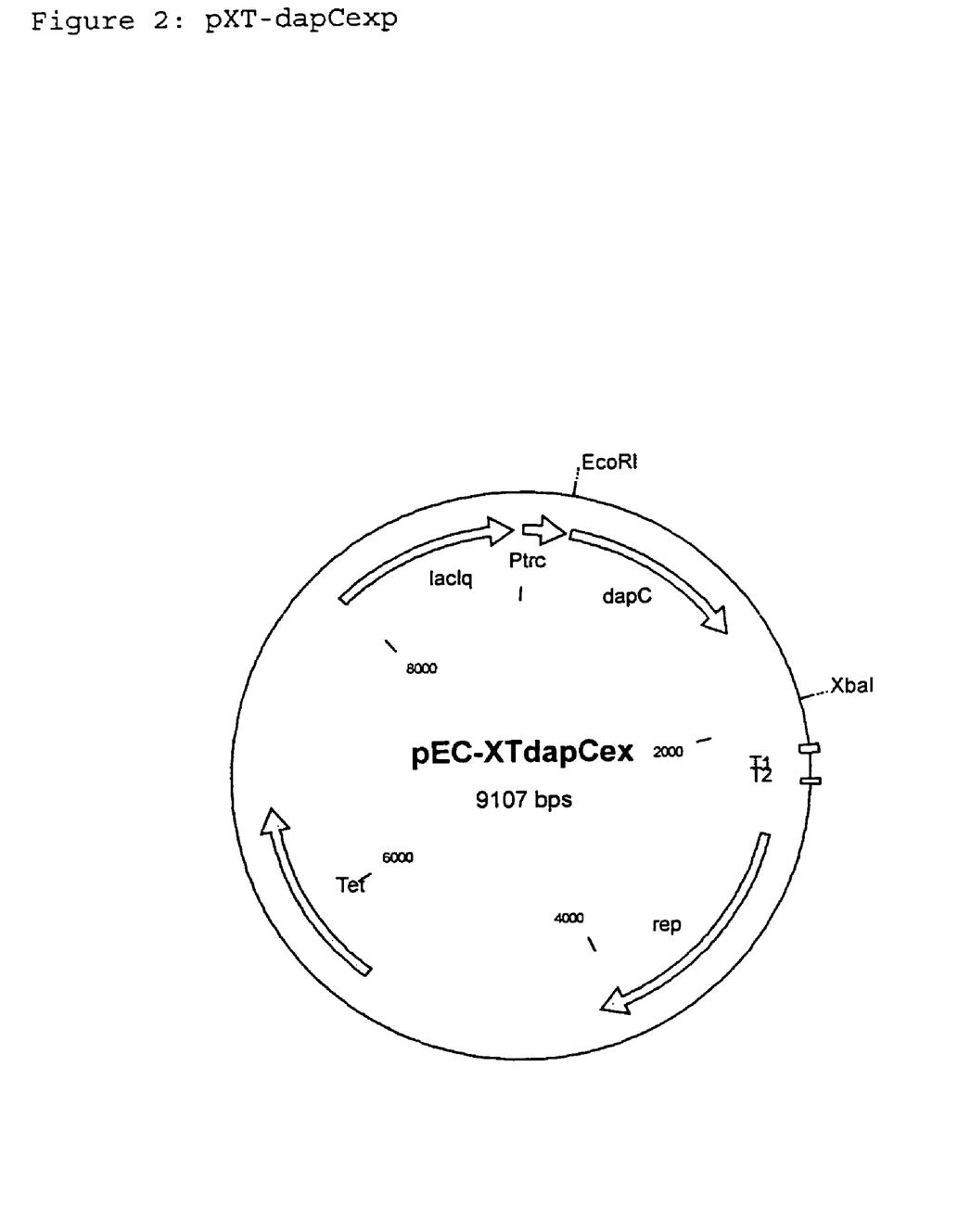

The invention also provides a polynucleotide according to claim 4, containing the nucleotide sequence as shown in SEQ ID no. 1, a polynucleotide which encodes a polypeptide which contains the amino acid sequence as shown in SEQ ID no. 2, a vector containing the polynucleotide according to claim 1, in particular a shuttle vector or the plasmid vector pXT-dapCexp, which is shown in FIG. 2 and is deposited under number DSM 13254 in DSM 5715.

and coryneform bacteria acting as host cell which contain the vector.

The invention also provides polynucleotides which substantially consist of a polynucleotide sequence, which are obtainable by screening by means of hybridization of a suitable gene library, which contains the complete gene having the polynucleotide sequence according to SEQ ID no. 1, with a probe which contains the sequence of the stated polynucleotide according to SEQ ID no. 1, or a fragment thereof, and isolation of the stated DNA sequence.

Polynucleotide sequences according to the invention are suitable as hybridization probes for RNA, cDNA and DNA in order to isolate full length cDNA which encode N-succinylaminoketopimelate transaminase and to isolate such cDNA or genes, the sequence of which exhibits a high level of similarity with that of the N-succinylaminoketopimelate transaminase gene.

Polynucleotide sequences according to the invention are furthermore suitable as primers for the production of DNA of genes which encode N-succinylaminoketopimelate transaminase by the polymerase chain reaction (PCR).

Such oligonucleotides acting as probes or primers contain at least 30, preferably at least 20, very particularly preferably at least 15 successive nucleotides. Oligonucleotides having a length of at least 40 or 50 nucleotides are also suitable.

"Isolated" means separated from its natural environment.

"Polynucleotide" generally relates to polyribonucleotides and polydeoxyribonucleotides, wherein the RNA or DNA may be unmodified or modified.

"Polypeptides" are taken to mean peptides or proteins which contain two or more amino acids connected by peptide bonds.

The polypeptides according to the invention include a polypeptide according to SEQ ID no. 2, in particular those having the biological activity of N-succinylaminoketopimelate transaminase and also those which are at least 70%, preferably at least 80%, identical to the polypeptide according to SEQ ID no. 2 and in particular are at least 90% to 95% identical to the polypeptide according to SEQ ID no. 2 and exhibit the stated activity.

The invention furthermore relates to a process for the fermentative production of amino acids, in particular L-lysine, using coryneform bacteria, which in particular already produce an amino acid and in which the nucleotide sequences which encode the dapC gene are enhanced, in particular overexpressed.

In this connection, the term "enhancement" describes the increase in the intracellular activity of one or more enzymes in a microorganism, which enzymes are encoded by the corresponding DNA, for example by increasing the copy number of the gene or genes, by using a strong promoter or a gene or allele which encodes a corresponding enzyme having elevated activity and optionally by combining these measures.

The microorganisms, provided by the present invention, may produce L-amino acids, in particular L-lysine, from glucose, sucrose, lactose, fructose, maltose, molasses, starch, cellulose or from glycerol and ethanol. The microorganisms may comprise representatives of the coryneform bacteria in particular of the genus *Corynebacterium*. Within the genus *Corynebacterium*, the species *Corynebacterium glutamicum* may in particular be mentioned, which is known in specialist circles for its ability to produce L-amino acids.

Suitable strains of the genus *Corynebacterium*, in particular of the species *Corynebacterium glutamicum*, are for example the known wild type strains

*Corynebacterium glutamicum* ATCC13032
*Corynebacterium acetoglutamicum* ATCC15806
*Corynebacterium acetoacidophilum* ATCC13870
*Corynebacterium thermoaminogenes* FERM BP-1539
*Corynebacterium melassecola* ATCC17965
*Brevibacterium flavum* ATCC14067
*Brevibacterium lactofermentum* ATCC13869 and
*Brevibacterium divaricatum* ATCC14020 and L-lysine producing mutants or strains produced therefrom, such as for example

*Corynebacterium glutamicum* FERM-P 1709
*Brevibacterium flavum* FERM-P 1708
*Brevibacterium lactofermentum* FERM-P 1712
*Corynebacterium glutamicum* FERM-P 6463
*Corynebacterium glutamicum* FERM-P 6464
*Corynebacterium glutamicum* DSM5715
*Corynebacterium glutamicum* DSM12866 and
*Corynebacterium glutamicum* DM58-1

The inventors succeeded in isolating the novel dapC gene, which encodes the enzyme N-succinylaminoketopimelate transaminase (EC 2.6.1.17), from *C. glutamicum*.

The dapC gene, and also other genes from *C. glutamicum*, are isolated by initially constructing a gene library of this microorganism in *E. coli*. The construction of gene libraries is described in generally known textbooks and manuals. Examples which may be mentioned are the textbook by Winnacker, Gene und Klone, Eine Einführung in die Gentechnologie (Verlag Chemie, Weinheim, Germany, 1990) or the manual by Sambrook et al., Molecular Cloning, A Laboratory Manual (Cold Spring Harbor Laboratory Press, 1989). One very well known gene library is that of *E. coli* K-12 strain W3110, which was constructed by Kohara et al. (Cell 50, 495-508 (1987)) in λ-vectors. Bathe et al. (Molecular and General Genetics, 252:255-265, 1996) describe a gene library of *C. glutamicum* ATCC13032, which was constructed using the cosmid vector SuperCos I (Wahl et al., 1987, Proceedings of the National Academy of Sciences USA, 84:2160-2164) in *E. coli* K-12 strain NM554 (Raleigh et al., 1988, Nucleic Acids Research 16:1563-1575). Börmann et al. (Molecular Microbiology 6(3), 317-326, 1992)) also describe a gene library of *C. glutamicum* ATCC 13032, using cosmid pHC79 (Hohn and Collins, Gene 11, 291-298 (1980)). A gene library of *C. glutamicum* in *E. coli* may also be produced using plasmids such as pBR322 (Bolivar, Life Sciences, 25, 807-818 (1979)) or pUC9 (Vieira et al., 1982, Gene, 19:259-268). Suitable hosts are in particular those *E. coli* strains with restriction and recombination defects. One example of such a strain is the strain DH5αmcr, which has been described by Grant et al. (Proceedings of the National Academy of Sciences USA, 87 (1990) 4645-4649). The long DNA fragments cloned with the assistance of cosmids may then in turn be sub-cloned in usual vectors suitable for sequencing and then be sequenced, as described, for example, in Sanger et al. (Proceedings of the National Academy of Sciences of the United States of America, 74:5463-5467, 1977).

The novel DNA sequence from *C. glutamicum* which encodes the dapC gene and, as SEQ ID no. 1, is provided by the present invention, was obtained in this manner. The amino acid sequence of the corresponding protein was furthermore deduced from the above DNA sequence using the methods described above. SEQ ID no. 2 shows the resultant amino acid sequence of the product of the dapC gene.

Coding DNA sequences arising from SEQ ID no. 1 due to the degeneracy of the genetic code are also provided by the invention. DNA sequences which hybridize with SEQ ID no. 1 or parts of SEQ ID no. 1 are also provided by the invention. Conservative substitutions of amino acids in proteins, for example the substitution of glycine for alanine or of aspartic acid for glutamic acid, are known in specialist circles as "sense mutations", which result in no fundamental change in activity of the protein, i.e. they are functionally neutral. It is furthermore known that changes to the N and/or C terminus of a protein do not substantially impair or may even stabilize the function thereof. The person skilled in the art will find information in this connection inter alia in Ben-Bassat et al. (Journal of Bacteriology 169:751-757 (1987)), in O'Regan et al. (Gene 77:237-251 (1989)), in Sahin-Toth et al. (Protein Sciences 3:240-247 (1994)), in Hochuli et al. (Bio/Technology 6:1321-1325 (1988)) and in known textbooks of genetics and molecular biology. Amino acid sequences arising in a corresponding manner from SEQ ID no. 2 are also provided by the invention.

Similarly, DNA sequences which hybridize with SEQ ID no. 1 or portions of SEQ ID no. 1 are also provided by the invention. Finally, DNA sequences produced by the polymerase chain reaction (PCR) using primers obtained from SEQ ID no. 1 are also provided by the invention. Such oligonucleotides typically have a length of at least 15 nucleotides.

The person skilled in the art may find instructions for identifying DNA sequences by means of hybridization inter alia in the manual "The DIG System Users Guide for Filter Hybridization" from Roche Diagnostics GmbH (Mannheim, Germany, 1993) and in Liebl et al. (International Journal of Systematic Bacteriology (1991) 41: 255-260). The person skilled in the art may find instructions for amplifying DNA sequences using the polymerase chain reaction (PCR) inter alia in the manual by Gait, Oligonucleotide Synthesis: A Practical Approach (IRL Press, Oxford, UK, 1984) and in Newton & Graham, PCR (Spektrum Akademischer Verlag, Heidelberg, Germany, 1994).

It has been found that coryneform bacteria produce L-lysine in an improved manner once the dapC gene has been over-expressed.

Over-expression may be achieved by increasing the copy number of the corresponding genes or by mutating the promoter and regulation region or the ribosome-binding site located upstream from the structural gene. Expression cassettes incorporated upstream from the structural gene act in the same manner. It is additionally possible to increase expression during fermentative L-lysine production by means of inducible promoters. Expression is also improved by measures to extend the lifetime of the mRNA. Enzyme activity is moreover enhanced by preventing degradation of the enzyme protein. The genes or gene constructs may either be present in plasmids in a variable copy number or be integrated in the chromosome and amplified. Alternatively, over-expression of the genes concerned may also be achieved by modifying the composition of the media and culture conditions.

The person skilled in the art will find guidance in this connection inter alia in Martin et al. (Bio/Technology 3, 137-146 (1987)), in Guerrero et al. (Gene 138, 35-41 (1994)), Tsuchiya and Morinaga (Bio/Technology 6, 428-430 (1988)), in Eikmanns et al. (Gene 102, 93-98 (1991)), in EP 0 472 869, in U.S. Pat. No. 4,601,893, in Schwarzer and Pühler (Bio/Technology 9, 84-87 (1991), in Reinscheid et al. (Applied and Environmental Microbiology 60, 126-132 (1994)), in LaBarre et al. (Journal of Bacteriology 175, 1001-1007 (1993)), in WO 96/15246, in Malumbres et al. (Gene 134, 15-24 (1993)), in JP-A-10-229891, in Jensen and Hammer (Biotechnology and Bioengineering 58, 191-195 (1998)), in Makrides (Microbiological Reviews 60:512-538 (1996)) and in known textbooks of genetics and molecular biology.

By way of example, the dapC gene according to the invention was over-expressed with the assistance of plasmids.

Suitable plasmids are those which are replicated in coryneform bacteria. Numerous known plasmid vectors, such as for example pZ1 (Menkel et al., Applied and Environmental Microbiology (1989) 64: 549-554), pEKEx1 (Eikmanns et al., Gene 102:93-98 (1991)) or pHS2-1 (Sonnen et al., Gene 107:69-74 (1991)) are based on the cryptic plasmids pHM1519, pBL1 or pGA1. Other plasmid vectors, such as for example those based on pCG4 (U.S. Pat. No. 4,489,160), or pNG2 (Serwold-Davis et al., FEMS Microbiology Letters 66, 119-124 (1990)), or pAG1 (U.S. Pat. No. 5,158,891) may be used in the same manner.

One example of a plasmid by means of which the dapC gene may be over-expressed is the E. coli-C. glutamicum shuttle vector pXT-dapCexp. The vector contains the replication region rep of plasmid pGA1, including the replication effector per (U.S. Pat. No. 5,175,108; Nesvera et al., Journal of Bacteriology 179, 1525-1532 (1997)), the tetA(Z) gene, which imparts tetracycline resistance, of plasmid pAG1 (U.S. Pat. No. 5,158,891; GenBank entry at the National Center for Biotechnology Information (NCBI, Bethesda, Md., USA) with the accession number AF121000), together with the replication origin, the trc promoter, the termination regions T1 and T2 and the lacI$^q$ gene (repressor of the lac operon of E. coli) of plasmid pTRC99A (Amann et al. (1988), Gene 69: 301-315).

The shuttle vector pXT-dapCexp is shown in FIG. 2.

Further suitable plasmid vectors are those with the assistance of which gene amplification may be performed by integration into the chromosome, as has for example been described by Reinscheid et al. (Applied and Environmental Microbiology 60, 126-132 (1994)) for the duplication or amplification of the hom-thrB operon. In this method, the complete gene is cloned into a plasmid vector which can replicate in a host (typically E. coli), but not in C. glutamicum. Vectors which may be considered are, for example, pSUP301 (Simon et al., Bio/Technology 1, 784-791 (1983)), pK18mob or pK19mob (Schäfer et al., Gene 145, 69-73 (1994)), pGEM-T (Promega corporation, Madison, Wis., USA), pCR2.1-TOPO (Shuman (1994). Journal of Biological Chemistry 269:32678-84; U.S. Pat. No. 5,487,993), pCR®Blunt (Invitrogen, Groningen, Netherlands; Bernard et al., Journal of Molecular Biology, 234: 534-541 (1993)) or pEM1 (Schrumpf et al, 1991, Journal of Bacteriology 173: 4510-4516). The plasmid vector which contains the gene to be amplified is then transferred into the desired strain of C. glutamicum by conjugation or transformation. The conjugation method is described, for example, in Schäfer et al. (Applied and Environmental Microbiology 60, 756-759 (1994)). Transformation methods are described, for example, in Thierbach et al. (Applied Microbiology and Biotechnology 29, 356-362 (1988)), Dunican and Shivnan (Bio/Technology 7, 1067-1070 (1989)) and Tauch et al. (FEMS Microbiological Letters 123, 343-347 (1994)). After homologous recombination by means of "crossing over", the resultant strain contains at least two copies of the gene in question.

It has furthermore been found that, by replacing the amino acid L-proline in position 209 of the enzyme protein (c.f. SEQ ID no. 2) with another proteinogenic amino acid, in particular L-leucine (c.f. SEQ ID no. 4), with the exception of L-proline, enhancement occurs and coryneform bacteria bearing the corresponding amino acid replacement produce L-lysine in an improved manner. The replacement of L-proline with L-leucine in position 209 may preferably be achieved by replacing the nucleobase cytosine in position 716 with thymine as shown in SEQ ID no. 3.

Mutagenesis may be performed by conventional mutagenesis methods using mutagens such as for example N-methyl-N'-nitro-N-nitrosoguanidine or ultraviolet light. Mutagenesis may also be performed by using in vitro methods such as for example treatment with hydroxylamine (Molecular and General Genetics 145, 101 pp (1978)) or mutagenic oligonucleotides (T. A. Brown: Gentechnologie für Einsteiger, Spektrum Akademischer Verlag, Heidelberg, 1993) or the polymerase chain reaction (PCR), as is described in the manual by Newton and Graham (PCR, Spektrum Akademischer Verlag, Heidelberg, 1994).

The invention accordingly also provides DNA originating from coryneform bacteria which encodes N-succinylaminoketopimelate transaminase, in which the amino acid sequence shown in SEQ ID no. 2 in position 209 is replaced with another amino acid, with the exception of L-proline. The invention also relates to coryneform bacteria which contain DNA in which the amino acid L-proline in position 209 of the enzyme protein (c.f. SEQ ID no. 2) is replaced with L-leucine (c.f. SEQ ID no. 4).

The invention furthermore provides coryneform bacteria which contain DNA in which the replacement of L-proline with L-leucine in position 209 proceeds by the replacement of the nucleobase cytosine in position 716 with thymine, as shown in SEQ ID no. 3.

It may additionally be advantageous for the production of L-lysine to amplify or over-express not only the dapC gene, but also one or more enzymes of the particular biosynthetic pathway, of glycolysis, of anaplerotic metabolism, or of amino acid export.

For the production of L-lysine, for example, it is thus possible in addition to the dapC gene simultaneously to enhance, in particular over-express or amplify, one or more genes selected from the group the lysC gene, which encodes a feed-back resistant aspartate kinase (Kalinowski et al. (1990), Molecular and General Genetics 224, 317-324), the asd gene, which encodes aspartate semialdehyde dehydrogenase (EP-A 0 219 027; Kalinowski et al. (1991), Molecular Microbiology 5:1197-1204, and Kalinowski et al. (1991), Molecular and General Genetics 224: 317-324), the dapA gene, which encodes dihydropicolinate synthase (EP-B 0 197 335), the dapB gene, which encodes dihydrodipicolinate reductase (GenBank entry accession number X67737; Pisabarro et al. (1993), Journal of Bacteriology, 175(9): 2743-2749), the dapD gene, which encodes tetrahydrodipicolinate succinylase (GenBank entry accession number AJ004934; Wehrmann et al. (1998), Journal of Bacteriology 180: 3159-3163), the dapE gene, which encodes N-succinyldiaminopimelate desuccinylase (GenBank entry accession number X81379; Wehrmann et al. (1994), Microbiology 140: 3349-3356), the dapF gene, which encodes diaminopimelate epimerase (DE: 199 43 587.1, DSM12968), the lysA gene, which encodes diaminopimelate decarboxylase (GenBank entry accession number X07563; Yeh et al. (1988), Molecular and General Genetics 212: 112-119), the ddh gene, which encodes diaminopimelate dehydrogenase (Ishino et al. (1988), Agricultural and Biological Chemistry 52(11): 2903-2909), the lysE gene, which encodes lysine export (DE-A-195 48 222), the pyc gene, which encodes pyruvate carboxylase (Eikmanns (1992), Journal of Bacteriology 174: 6076-6086), the mqo gene, which encodes malate:quinone oxidoreductase (Molenaar et al. (1998), European Journal of Biochemistry 254: 395-403), the zwa1 gene (DE: 19959328.0, DSM 13115), the gdh gene, which encodes glutamate dehydrogenase (Börmann et al. (1992), Molecular Microbiology 6, 317-326).

It is preferred simultaneously to enhance one or more genes selected from the group dapD, dapE and dapF.

It may furthermore be advantageous for the production of L-lysine, in addition to enhancing the dapC gene, optionally in combination with one or more genes selected from the group dapD, dapE and dapF, simultaneously to attenuate the pck gene, which encodes phosphoenolpyruvate carboxykinase (DE 199 50 409.1, DSM 13047) or the pgi gene, which encodes glucose 6-phosphate isomerase (U.S. Ser. No. 09/396,478, DSM 12969), or the poxB gene, which encodes pyruvate oxidase (DE: 19951975.7, DSM 13114), or the zwa2 gene (DE: 19959327.2, DSM 13113), or the sucC or sucD genes which encode succinyl CoA synthetase (DE: 19956686.0).

It may furthermore be advantageous for the production of L-lysine, in addition to enhancing the dapC gene, optionally in combination with one or more genes selected from the group dapD, dapE and dapF, to suppress unwanted secondary reactions (Nakayama: "Breeding of Amino Acid Producing Micro-organisms", in: Over-production of Microbial Products, Krumphanzl, Sikyta, Vanek (eds.), Academic Press, London, UK, 1982).

For the purposes of L-lysine production, the microorganisms produced according to the invention may be cultured continuously or discontinuously using the batch process or the fed batch process or repeated fed batch process. A summary of known culture methods is given in the textbook by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used must adequately satisfy the requirements of the particular strains. Culture media for various microorganisms are described in "Manual of Methods for General Bacteriology" from the American Society for Bacteriology (Washington D.C., USA, 1981).

Carbon sources which may be used are sugars and carbohydrates, such as glucose, sucrose, lactose, fructose, maltose, molasses, starch and cellulose for example, oils and fats, such as soya oil, sunflower oil, peanut oil and coconut oil for example, fatty acids, such as palmitic acid, stearic acid and linoleic acid for example, alcohols, such as glycerol and ethanol for example, and organic acids, such as acetic acid for example. These substances may be used individually or as a mixture.

Nitrogen sources which may be used comprise organic compounds containing nitrogen, such as peptones, yeast extract, meat extract, malt extract, corn steep liquor, soya flour and urea or inorganic compounds, such as ammonium sulfate, ammonium chloride, ammonium phosphate, ammonium carbonate and ammonium nitrate. The nitrogen sources may be used individually or as a mixture.

Phosphorus sources which may be used are phosphoric acid, potassium dihydrogen phosphate or dipotassium hydrogen phosphate or the corresponding salts containing sodium. The culture medium has additionally to contain salts of metals, such as magnesium sulfate or iron sulfate for example, which are necessary for growth. Finally, essential growth-promoting substances such as amino acids and vitamins may also be used in addition to the above-stated substances. Suitable precursors may furthermore be added to the culture medium. The stated feed substances may be added to the culture as a single batch or be fed appropriately during culturing.

Basic compounds, such as sodium hydroxide, potassium hydroxide, ammonia or ammonia water, or acidic compounds, such as phosphoric acid or sulfuric acid, are used appropriately to control the pH of the culture. Foaming may be controlled by using antifoaming agents such as fatty acid polyglycol esters for example. Plasmid stability may be maintained by the addition to the medium of suitable selectively acting substances, for example antibiotics. Oxygen or oxygen-containing gas mixtures, such as air for example, are introduced into the culture in order to maintain aerobic conditions. The temperature of the culture is normally from 20° C. to 45° C. and preferably from 25° C. to 40° C. The culture is continued until the maximum quantity of lysine has formed. This aim is normally achieved within 10 to 160 hours.

Analysis of L-lysine may be performed by anion exchange chromatography with subsequent ninhydrin derivation, as described in Spackman et al. (Analytical Chemistry, 30, (1958), 1190).

The following microorganism has been deposited with Deutsche Sammlung für Mikroorganismen und Zellkulturen (DSMZ, Braunschweig, Germany) in accordance with the Budapest Treaty:

*Corynebacterium glutamicum* strain DSM5715/pXT-dapCexp as DSM 13254.

BRIEF DESCRIPTION OF THE DRAWINGS

FIG. 2: Map of plasmid pXT-dapCexp
The abbreviations and names are defined as follows.
per: Gene for controlling copy number from pGA1
oriE: Plasmid-coded replication origin of *E. coli*
rep: Plasmid-coded replication origin from *C. glutamicum* plasmid pGA1
Ptrc: trc promoter from pTRC99A
T1, T2: Terminator regions 1 and 2 from pTRC99A
lacIq: Repressor gene of the Lac operon
Tet: Resistance gene for tetracycline
dapC: dapC gene from *C. glutamicum*
EcoRI: Restriction site of the restriction enzyme EcoRI
EcoRV: Restriction site of the restriction enzyme EcoRV
HindIII: Restriction site of the restriction enzyme HindIII
KpnI: Restriction site of the restriction enzyme KpnI
SalI: Restriction site of the restriction enzyme SalI
SmaI: Restriction site of the restriction enzyme SmaI
NdeI: Restriction site of the restriction enzyme NdeI
BamHI: Restriction site of the restriction enzyme BamHI
NcoI: Restriction site of the restriction enzyme NcoI
XbaI: Restriction site of the restriction enzyme XbaI
SacI: Restriction site of the restriction enzyme SacI

DETAILED DESCRIPTION OF THE INVENTION

The present invention is illustrated in greater detail by the following practical examples.

Example 1

Production of a Genomic Cosmid Gene Library from *Corynebacterium glutamicum* ATCC 13032

Chromosomal DNA from *Corynebacterium glutamicum* ATCC 13032 was isolated as described in Tauch et al., (1995, Plasmid 33:168-179) and partially cleaved with the restriction enzyme Sau3AI (Amersham Pharmacia, Freiburg, Germany, product description Sau3AI, code no. 27-0913-02). The DNA fragments were dephosphorylated with shrimp alkaline phosphatase (Roche Diagnostics GmbH, Mannheim, Germany, product description SAP, code no. 1758250). The DNA of cosmid vector SuperCos1 (Wahl et al. (1987) Proceedings of the National Academy of Sciences USA 84:2160-2164), purchased from Stratagene (La Jolla, USA, product description SuperCos1 Cosmid Vector Kit, code no. 251301) was cleaved with the restriction enzyme XbaI (Amersham Pharmacia, Freiburg, Germany, product description XbaI, code no. 27-0948-02) and also dephosphorylated with shrimp alkaline phosphatase. The cosmid DNA was then cleaved with the restriction enzyme BamHI (Amersham Pharmacia, Freiburg, Germany, product description BamHI, code no. 27-0868-04). Cosmid DNA treated in this manner was mixed with the treated ATCC 13032 DNA and the batch was treated with T4 DNA ligase (Amersham Pharmacia, Freiburg, Germany, product description T4 DNA Ligase, code no. 27-0870-04). The ligation mixture was then packed in phages using Gigapack II XL Packing Extracts (Stratagene, La Jolla, USA, product description Gigapack II XL Packing Extract, code no. 200217). *E. coli* strain NM554 (Raleigh et al. 1988, Nucleic Acid Research 16:1563-1575) was infected by suspending the cells in 10 mM MgSO$_4$ and mixing them with an aliquot of the phage suspension. The cosmid library was infected and titred as described in Sambrook et al. (1989, Molecular Cloning: A Laboratory Manual, Cold Spring Harbor), the cells being plated out on LB agar (Lennox, 1955, Virology, 1:190) with 100 mg/l of ampicillin. After overnight incubation at 37° C., individual recombinant clones were selected.

Example 2

Isolation and Sequencing of the dapC Gene

Cosmid DNA from an individual colony was isolated in accordance with the manufacturer's instructions using the Qiaprep Spin Miniprep Kit (product no. 27106, Qiagen, Hilden, Germany) and partially cleaved with the restriction enzyme Sau3AI (Amersham Pharmacia, Freiburg, Germany, product description Sau3AI, product no. 27-0913-02). The DNA fragments were dephosphorylated with shrimp alkaline phosphatase (Roche Diagnostics GmbH, Mannheim, Germany, product description SAP, product no. 1758250). Once separated by gel electrophoresis, the cosmid fragments of a size of 1500 to 2000 bp were isolated using the QiaExII Gel Extraction Kit (product no. 20021, Qiagen, Hilden, Germany). The DNA of the sequencing vector pZero-1 purchased from Invitrogen (Groningen, Netherlands, product description Zero Background Cloning Kit, product no. K2500-01) was cleaved with the restriction enzyme BamHI (Amersham Pharmacia, Freiburg, Germany, product description BamHI, product no. 27-0868-04). Ligation of the cosmid fragments into the sequencing vector pZero-1 was performed as described by Sambrook et al. (1989, Molecular Cloning: A Laboratory Manual, Cold Spring Harbor), the DNA mixture being incubated overnight with T4 ligase (Pharmacia Biotech, Freiburg, Germany). This ligation mixture was then electroporated into the *E. coli* strain DH5αMCR (Grant, 1990, Proceedings of the National Academy of Sciences U.S.A., 87:4645-4649) (Tauch et al. 1994, FEMS Microbiol Letters, 123:343-7) and plated out onto LB agar (Lennox, 1955, Virology, 1:190) with 50 mg/l of Zeocin. Plasmids of the recombinant clones were prepared using the Biorobot 9600 (product no. 900200, Qiagen, Hilden, Germany). Sequencing was performed using the dideoxy chain termination method according to Sanger et al. (1977, Proceedings of the National Academies of Sciences U.S.A., 74:5463-5467) as modified by Zimmermann et al. (1990, Nucleic Acids Research, 18:1067). The "RR dRhodamin Terminator Cycle Sequencing Kit" from PE Applied Biosystems (product no. 403044, Weiterstadt, Germany) was used. Separation by gel electrophoresis and analysis of the sequencing reaction was performed in a "Rotiphorese NF" acrylamide/bisacrylamide gel (29:1) (product no. A124.1, Roth, Karlsruhe, Germany) using the "ABI Prism 377" sequencer from PE Applied Biosystems (Weiterstadt, Germany).

The resultant raw sequence data were then processed using the Staden software package (1986, Nucleic Acids Research, 14:217-231), version 97-0. The individual sequences of the pZero1 derivatives were assembled into a cohesive contig. Computer-aided coding range analysis was performed using XNIP software (Staden, 1986, Nucleic Acids Research, 14:217-231). Further analysis was performed using the "BLAST search programs" (Altschul et al., 1997, Nucleic Acids Research, 25:3389-3402), against the non-redundant database of the "National Center for Biotechnology Information" (NCBI, Bethesda, Md., USA).

The resultant nucleotide sequence of the dapC gene is stated in SEQ ID no. 1. Analysis of the nucleotide sequence revealed an open reading frame of 1101 base pairs, which was designated the dapC gene. The dapC gene encodes a polypeptide of 367 amino acids, which is shown in SEQ ID no. 2.

Example 3

Production of a Shuttle Vector pXT-dapCexp for Enhancing the dapC Gene in *C. glutamicum*

3.1. Cloning of the dapC Gene

Chromosomal DNA was isolated from strain ATCC 13032 using the method of Eikmanns et al. (Microbiology 140: 1817-1828 (1994)). On the basis of the sequence of the dapC gene for *C. glutamicum* known from Example 2, the following oligonucleotides were selected for the polymerase chain reaction (c.f. also SEQ ID no. 5 and 6):

DapC (dCex1):

5' GAT CTA (GAA TTC) GCC TCA GGC ATA ATC TAA CG 3'

DapC (dCexna2):

5' GAT CTA (TCT AGA) CAG AGG ACA AGG CAA TCG GA 3'

The stated primers were synthesized by the company ARK Scientific GmbH Biosystems (Darmstadt, Germany) and the PCR reaction performed in accordance with the standard PCR method of Innis et al. (PCR Protocols. A Guide to Methods and Applications, 1990, Academic Press) using Pwo polymerase from Roche Diagnostics GmbH (Mannheim, Germany). By means of the polymerase chain reaction, the primers permit the amplification of an approx. 1.6 kb DNA fragment, which bears the dapC gene. Moreover, the primer DapC (dCex1) contains the sequence for the restriction site of the restriction endonuclease EcoRI, and the primer DapC (dCexna2) contains the restriction site of the restriction endonuclease XbaI, which are indicated between brackets in the above-stated nucleotide sequence.

The amplified approx. 1.6 kb DNA fragment, which bears the dapC gene, was ligated into the vector pCR®Blunt II (Bernard et al., Journal of Molecular Biology, 234:534-541 (1993)) using the Zero Blunt™ Kit from Invitrogen Corporation (Carlsbad, Calif., USA; catalogue number K2700-20). The *E. coli* strain Top10 was then transformed with the ligation batch in accordance with the kit manufacturer's instructions (Invitrogen Corporation, Carlsbad, Calif., USA). Plasmid-bearing cells were selected by plating the transformation batch out onto LB agar (Sambrook et al., Molecular Cloning: A Laboratory Manual, 2$^{nd}$ Ed., Cold Spring Harbor Laboratory Press, Cold Spring Harbor, N.Y., 1989) which had been supplemented with 25 mg/l of kanamycin. Plasmid DNA was isolated from a transformant using the QIAprep Spin Miniprep Kit from Qiagen (Hilden, Germany) and verified by restriction with the restriction enzymes XbaI and EcoRI and subsequent (0.8%) agarose gel electrophoresis. The DNA sequence of the amplified DNA fragment was verified by sequencing. The plasmid was named pCRdapC. The strain was designated *E. coli* Top10/pCRdapC.

3.2. Production of the *E. coli-C. glutamicum* Shuttle Vector pEC-XT99A

The *E. coli* expression vector pTRC99A (Amann et al. 1988, Gene 69:301-315) was used as the starting vector for constructing the *E. coli-C. glutamicum* shuttle expression vector pEC-XT99A. After BspHI restriction cleavage (Roche Diagnostics GmbH, Mannheim, Germany, production description BspHI, product no. 1467123) and subsequent Klenow treatment (Amersham Pharmacia Biotech, Freiburg, Germany, product description Klenow Fragment of DNA Polymerase I, product no. 27-0928-01; method according to Sambrook et al., 1989, Molecular Cloning: A Laboratory Manual, Cold Spring Harbor), the ampicillin resistance gene (bla) was replaced by the tetracycline resistance gene of *C. glutamicum* plasmid pAG1 (GenBank accession no. AF121000). To this end, the region bearing the resistance gene was cloned as an AluI fragment (Amersham Pharmacia Biotech, Freiburg, Germany, product description AluI, product no. 27-0884-01) into the linearized *E. coli* expression vector pTRC99A. Ligation was performed as described by Sambrook et al. (1989, Molecular Cloning: A Laboratory Manual, Cold Spring Harbor), the DNA mixture being incubated overnight with T4 ligase (Amersham Pharmacia Biotech, Freiburg, Germany, product description T4 DNA Ligase, product no. 27-0870-04). This ligation mixture was then electroporated into the *E. coli* strain DH5αmcr (Grant, 1990, Proceedings of the National Academy of Sciences U.S.A., 87:4645-4649) (Tauch et al. 1994, FEMS Microbiol Letters, 123:343-7). The constructed *E. coli* expression vector was designated pXT99A.

Plasmid pGA1 (Sonnen et al. 1991, Gene, 107:69-74) was used as the basis for cloning a minimal replicon from *Corynebacterium glutamicum*. By means of BalI/PstI restriction cleavage (Promega GmbH, Mannheim, Germany, production description BalI, product no. R6691; Amersham Pharmacia Biotech, Freiburg, Germany, production description PstI, product no. 27-0976-01) of the pGA1 vector, it proved possible to clone a 3484 bp fragment into the pK18mob2 vector (Tauch et al., 1998, Archives of Microbiology 169:303-312) which had been fragmented with SmaI und PstI (Amersham Pharmacia Biotech, Freiburg, Germany, product description SmaI, product no. 27-0942-02, product description PstI, product no. 27-0976-01). An 839 bp fragment was deleted by BamHI/XhoI restriction cleavage (Amersham Pharmacia Biotech, Freiburg, Germany, product description BamHI, product no. 27-086803, product description XhoI, product no. 27-0950-01) and subsequent Klenow treatment (Amersham Pharmacia Biotech, Freiburg, Germany, product description Klenow Fragment of DNA Polymerase I, product no. 27-0928-01; method according to Sambrook et al., 1989, Molecular Cloning: A Laboratory Manual, Cold Spring Harbor). The *C. glutamicum* minimal replicon could be cloned into the *E. coli* expression vector pXT99A as a 2645 bp fragment from the construct which had been religated with T4 ligase (Amersham Pharmacia Biotech, Freiburg, Germany, product description T4 DNA Ligase, product no. 27-0870-04). To this end, the DNA of the construct bearing the minimal replicon was cleaved with the restriction enzymes KpnI (Amersham Pharmacia Biotech, Freiburg, Germany, product description KpnI, product no. 27-0908-01) and PstI (Amersham Pharmacia Biotech, Freiburg, Germany, product description PstI, product no. 27-0886-03) and then a 3'-5'-exonuclease treatment (Sambrook et al., 1989, Molecular Cloning: A Laboratory Manual, Cold Spring Harbor) was performed by means of Klenow polymerase (Amersham Pharmacia Biotech, Freiburg, Germany, product description Klenow Fragment of DNA Polymerase I, product no. 27-0928-01).

In a parallel batch, the *E. coli* expression vector pXT99A was cleaved with the restriction enzyme RsrII (Roche Diagnostics, Mannheim, Germany, product description RsrII, product no. 1292587) and prepared for ligation with Klenow polymerase (Amersham Pharmacia Biotech, Freiburg, Germany, Klenow Fragment of DNA Polymerase I, product no.

27-0928-01). Ligation of the minimal replicon with the vector construct pXT99A was performed as described by Sambrook et al. (1989, Molecular Cloning: A Laboratory Manual, Cold Spring Harbor), the DNA mixture being incubated overnight with T4 ligase (Amersham Pharmacia Biotech, Freiburg, Germany, product description T4 DNA Ligase, product no. 27-0870-40).

The *E. coli-C. glutamicum* shuttle expression vector pEC-XT99A constructed in this manner was transferred into *C. glutamicum* DSM5715 by electroporation (Liebl et al., 1989, FEMS Microbiology Letters, 53:299-303). Transformant selection proceeded on LBHIS agar consisting of 18.5 g/l of brain-heart infusion bouillon, 0.5 M sorbitol, 5 g/l of Bacto tryptone, 2.5 g/l of Bacto yeast extract, 5 g/l of NaCl and 18 g/l of Bacto agar, which had been supplemented with 5 mg/l of tetracycline. Incubation was performed for 2 days at 33° C.

Plasmid DNA was isolated from a transformant using the conventional methods (Peters-Wendisch et al., 1998, Microbiology, 144, 915-927), cut with the restriction endonuclease HindIII and the plasmid verified by subsequent agarose gel electrophoresis.

Figure 1:
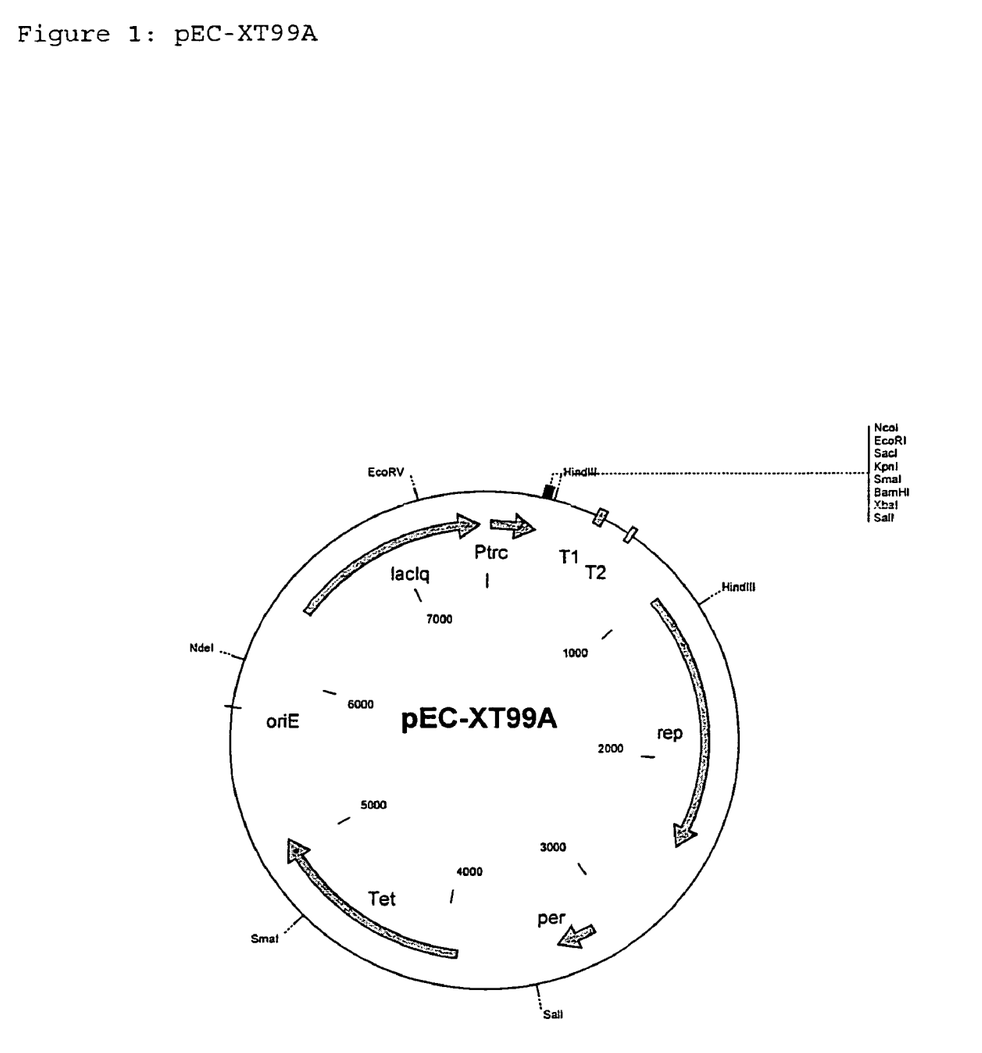
FIG. 1: Map of plasmid pEC-XT99A

The resultant plasmid construct was named pEC-XT99A and is shown in FIG. 1. The strain obtained by electroporation of plasmid pEC-XT99A into *Corynebacterium glutamicum* DSM5715 was named DSM5715/pEC-XT99A and has been deposited with Deutsche Sammlung für Mikroorganismen und Zellkulturen (DSMZ, Braunschweig, Germany) in accordance with the Budapest Treaty.

3.3. Cloning of dapC in the *E. coli-C. glutamicum* Shuttle Vector pEC-XT99A

The vector used was the *E. coli-C. glutamicum* shuttle vector pEC-XT99A described in Example 3.2. DNA from this plasmid was completely cleaved with the restriction enzymes EcoRI and XbaI and then dephosphorylated with shrimp alkaline phosphatase (Roche Diagnostics GmbH, Mannheim, Germany, product description SAP, product no. 1758250).

The dapC gene was isolated from the plasmid pCRdapC described in Example 3.1. by complete cleavage with the enzymes EcoRI and XbaI. The approx. 1600 bp dapC fragment was isolated from the agarose gel using the QiaExII Gel Extraction Kit (product no. 20021, Qiagen, Hilden, Germany).

The dapC fragment obtained in this manner was mixed with the prepared pEC-XT99A vector and the batch was treated with T4 DNA ligase (Amersham Pharmacia, Freiburg, Germany, product description T4 DNA Ligase, code no. 27-0870-04). The ligation batch was then transformed into *E. coli* strain DH5α (Hanahan, in: DNA Cloning. A Practical Approach, Vol. I, IRL-Press, Oxford, Washington D.C., USA). Plasmid-bearing cells were selected by plating the transformation batch out onto LB agar (Lennox, 1955, Virology, 1:190) with 5 mg/l of tetracycline. After overnight incubation at 37° C., individual recombinant clones were selected. Plasmid DNA was isolated from a transformant in accordance with the manufacturer's instructions using the Qiaprep Spin Miniprep Kit (product no. 27106, Qiagen, Hilden, Germany) and cleaved with the restriction enzymes EcoRI and XbaI in order to verify the plasmid by subsequent agarose gel electrophoresis. The resultant plasmid was named pXT-dapCexp. It is shown in FIG. 2.

Example 4

Transformation of Strain DSM5715 with Plasmid pXT-dapCexp

Strain DSM5715 was then transformed with plasmid pXT-dapCexp using the electroporation method described by Liebl et al. (FEMS Microbiology Letters, 53:299-303 (1989)). Transformant selection proceeded on LBHIS agar consisting of 18.5 g/l of brain-heart infusion bouillon, 0.5 M sorbitol, 5 g/l of Bacto tryptone, 2.5 g/l of Bacto yeast extract, 5 g/l of NaCl and 18 g/l of Bacto agar, which had been supplemented with 5 mg/l of tetracycline. Incubation was performed for 2 days at 33° C.

Plasmid DNA was isolated from a transformant using the conventional method (Peters-Wendisch et al., 1998, Microbiology, 144, 915-927), cut with the restriction endonucleases EcoRI and XbaI and the plasmid was verified by subsequent agarose gel electrophoresis. The resultant strain was named DSM715/pXT-dapCexp and has been deposited as DSM 13254 (on Jan. 20, 2000) with Deutsche Sammlung für Mikroorganismen und Zellkulturen (DSMZ GmbH, Mascheroder Weg 1b. D-38124, Braunschweig, Germany).

Example 5

Production of L-Lysine

The *C. glutamicum* strain DSM5715/pXT-dapCexp obtained in Example 4 was cultured in a nutrient medium suitable for the production of lysine and the lysine content of the culture supernatant was determined.

To this end, the strain was initially incubated for 24 hours at 33° C. on an agar plate with the appropriate antibiotic (brain/heart agar with tetracycline (5 mg/l)). Starting from this agar plate culture, a preculture was inoculated (10 ml of medium in a 100 ml Erlenmeyer flask). The complete medium CgIII was used as the medium for this preculture.

| Medium Cg III | |
|---|---|
| NaCl | 2.5 g/l |
| Bacto peptone | 10 g/l |
| Bacto yeast extract | 10 g/l |
| Glucose (separately autoclaved) | 2% (w/v) |

The pH value was adjusted to pH 7.4.

Tetracycline (5 mg/l) was added to this medium. The preculture was incubated for 16 hours at 33° C. on a shaker at 240 rpm. A main culture was inoculated from this preculture, such that the initial OD (660 nm) of the main culture was 0.1. Medium MM was used for the main culture.

| Medium MM | |
|---|---|
| CSL (Corn Steep Liquor) | 5 g/l |
| MOPS (morpholinopropanesulfonic acid) | 20 g/l |
| Glucose (separately autoclaved) | 50 g/l |
| $(NH_4)_2SO_4$ | 25 g/l |
| $KH_2PO_4$ | 0.1 g/l |

-continued

| Medium MM | |
|---|---|
| MgSO$_4$*7 H$_2$O | 1.0 g/l |
| CaCl$_2$*2 H$_2$O | 10 mg/l |
| FeSO$_4$*7 H$_2$O | 10 mg/l |
| MnSO$_4$*H$_2$O | 5.0 mg/l |
| Biotin (sterile-filtered) | 0.3 mg/l |
| Thiamine*HCl (sterile-filtered) | 0.2 mg/l |
| L-leucine (sterile-filtered) | 0.1 g/l |
| CaCO$_3$ | 25 g/l |

CSL, MOPS and the salt solution were adjusted to pH 7 with ammonia water and autoclaved. The sterile substrate and vitamin solutions, together with the dry-autoclaved CaCO$_3$ are then added.

Culturing is performed in a volume of 10 ml in a 100 ml Erlenmeyer flask with flow spoilers. Tetracycline (5 mg/l) was added. Culturing was performed at 33° C. and 80% atmospheric humidity.

After 72 hours, the OD was determined at a measurement wavelength of 660 nm using a Biomek 1000 (Beckmann Instruments GmbH, Munich). The quantity of lysine formed was determined using an amino acid analyzer from Eppendorf-BioTronik (Hamburg, Germany) by ion exchange chromatography and post-column derivation with ninhydrin detection.

Table 1 shows the result of the test.

TABLE 1

| Strain | OD (660 nm) | Lysine HCl 25 g/l |
|---|---|---|
| DSM5715 | 7.0 | 13.7 |
| DSM5715/pXT-dapCexp | 7.1 | 14.7 |

What is claimed is:

1. A process for the production of L-lysine, comprising the following steps:
   a) fermenting coryneform bacteria producing L-lysine in which at least the dapC gene is overexpressed,
   b) allowing accumulation of the L-lysine in the medium or in the cells of the bacteria, and
   c) isolating the L-lysine,
   wherein the dapC gene comprises a polynucleotide sequence encoding a polypeptide sequence comprising the sequence of SEQ ID NO: 2 wherein the amino acid in position 209 of SEQ ID NO: 2 can be any proteinogenic amino acid, and the polypeptide has the activity of N-succinyl-aminoketopimelate-transaminase.

2. The process according to claim 1, wherein the encoded polypeptide sequence is identical to SEQ ID NO:2.

3. The process according to claim 1, wherein said polynucleotide sequence comprises the sequence from position 91 to 1191 of SEQ ID NO: 1.

4. The process according to claim 1, wherein said polynucleotide sequence comprises the sequence of SEQ ID NO: 1.

5. The process according to claim 1, wherein the coryneform bacteria are fermented for the production of L-lysine, in which, in addition to the dapC gene, one or more Corynebacterium glutamicum genes selected from the group consisting of,
   (a) the lysC gene, which encodes an aspartate kinase,
   (b) the asd gene, which encodes aspartate semialdehyde dehydrogenase,
   (c) the dapA gene, which encodes dihydropicolinate synthase,
   (d) the dapB gene, which encodes dihydrodipicolinate reductase,
   (e) the dapD gene, which encodes tetrahydropicolinate succinylase,
   (f) the dapE gene, which encodes N-succinyldiaminopimelate desuccinylase,
   (g) the dapF gene, which encodes diaminopimelate epimerase,
   (h) the lysA gene, which encodes diaminopimelate decarboxylase,
   (i) the ddh gene, which encodes diaminopimelate dehydrogenase,
   (j) the lysE gene, which encodes a lysine export protein,
   (k) the pyc gene, which encodes pyruvate carboxylase,
   (l) the mqo gene, which encodes malate: quinone oxidoreductase, (m) the gdh gene, which encodes glutamate dehydrogenase, are over-expressed.

6. The process according to claim 1, wherein microorganisms of the genus *Corynebacterium glutamicum* are used.

7. A process according to claim 5, wherein microorganisms of the genus *Corynebacterium glutamicum* are used.

8. A process according to claim 5, wherein the dapA gene is overexpressed.

9. A process according to claim 1, wherein said encoded polypeptide sequence is identical to SEQ ID NO:4.

* * * * *